United States Patent
Sandvik et al.

(10) Patent No.: US 7,053,425 B2
(45) Date of Patent: May 30, 2006

(54) GAS SENSOR DEVICE

(75) Inventors: Peter Micah Sandvik, Guilderland, NY (US); Vinayak Tilak, Watervliet, NY (US); Jesse Tucker, Niskayuna, NY (US); Stanton Earl Weaver, Northville, NY (US); David Mulford Shaddock, Troy, NY (US); Jonathan Lloyd Male, Schoharie, NY (US); John Patrick Lemmon, Schoharie, NY (US); Mark Allen Woodmansee, Schenectady, NY (US); Venkatesan Manivannan, Rexford, NY (US); Deborah Ann Haitko, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/706,767

(22) Filed: Nov. 12, 2003

(65) Prior Publication Data

US 2005/0097941 A1     May 12, 2005

(51) Int. Cl.
*H01L 31/312*   (2006.01)
*G01N 27/12*   (2006.01)
(52) U.S. Cl. ............... 257/253; 438/46; 73/31.06
(58) Field of Classification Search .......... 257/253; 438/46; 73/31.06
See application file for complete search history.

(56) References Cited

U.S. PATENT DOCUMENTS

| | | | |
|---|---|---|---|
| 3,951,603 A | * | 4/1976 | Obayashi et al. ........... 436/131 |
| 4,816,800 A | * | 3/1989 | Onaga et al. ................. 338/34 |
| 4,931,851 A | * | 6/1990 | Sibbald et al. ............... 257/414 |
| 5,285,084 A | * | 2/1994 | von Windheim et al. ..... 257/77 |
| 5,362,975 A | * | 11/1994 | von Windheim et al. ..... 257/76 |
| 5,417,821 A | | 5/1995 | Pyke |
| 5,591,321 A | | 1/1997 | Pyke |
| 5,656,827 A | * | 8/1997 | Kang et al. ................... 257/76 |
| 5,698,771 A | * | 12/1997 | Shields et al. ............. 73/31.05 |
| 5,942,676 A | * | 8/1999 | Potthast et al. ............ 73/31.06 |
| 6,041,643 A | | 3/2000 | Stokes et al. |
| 6,109,094 A | * | 8/2000 | Baranzahi et al. ......... 73/31.06 |
| 6,140,144 A | * | 10/2000 | Najafi et al. ................. 438/53 |

(Continued)

FOREIGN PATENT DOCUMENTS

DE  19960798  7/2001

(Continued)

OTHER PUBLICATIONS

Schalwig et al., "Gas sensitive GaN/AlGaN-heterostructures", Sensors and Actuators B, 2002, vol. 87, pp. 425-530.*

(Continued)

*Primary Examiner*—Michael Cygan
(74) *Attorney, Agent, or Firm*—William E. Powell, III; Christian G. Cabou

(57) ABSTRACT

A gas sensor device including a semiconductor substrate; one or more catalytic gate-electrodes deposited on a surface of the semiconductor substrate; one or more ohmic contacts deposited on the surface of the semiconductor substrate and a passivation layer deposited on at least a portion of the surface; wherein the semiconductor substrate includes a material selected from the group consisting of silicon carbide, diamond, Group III nitrides, alloys of Group III nitrides, zinc oxide, and any combinations thereof.

41 Claims, 6 Drawing Sheets

U.S. PATENT DOCUMENTS

| | | | |
|---|---|---|---|
| 6,155,100 | A | 12/2000 | Stokes et al. |
| 6,182,500 | B1 | 2/2001 | Stokes et al. |
| 6,202,473 | B1 | 3/2001 | Stokes et al. |
| 6,278,133 | B1 | 8/2001 | Harris et al. |
| 6,291,838 | B1 | 9/2001 | Hunter |
| 6,298,710 | B1 | 10/2001 | Samman et al. |
| 6,378,355 | B1 | 4/2002 | Samman et al. |
| 6,418,784 | B1 | 7/2002 | Samman et al. |
| 6,474,139 | B1 | 11/2002 | Samman et al. |
| 6,690,042 | B1 * | 2/2004 | Khan et al. ............... 257/192 |
| 2004/0112764 | A1 | 6/2004 | Stokes et al. |

FOREIGN PATENT DOCUMENTS

| | | |
|---|---|---|
| DE | 100 32 062 | 1/2002 |
| DE | 10031549 | 1/2002 |
| DE | 10032062 | 1/2002 |
| EP | 0737859 | 10/2001 |

OTHER PUBLICATIONS

Spetz et al., "SiC Based Field Effect Gas Sensors for Industrial Applications", Phys. Stat. Sol. A, 2001, vol. 185, No. 1, pp. 15-25.*

A. Trinchi, et al.; "A Pt/$Ga_2O_3$-ZnO/SiC Schottsky Diode-Based Hydrocarbon Gas Sensor" IEEE Sensors Journal, vol. 3. No. 5 Oct. 2003; p. 548-553.

P. Tobias, et al.; "Interface States in High-Temperature Gas Sensors Based on Silicon Carbide" IEEE Sensors Journal, vol. 2. No. 5 Oct. 2003; p. 543-547.

J. Schalwig et al., *"Gas Sensitive GaN/AlGaN-Heterostructures"*, Elsevier, Sensors and Actuators, B87, pp. 425-430, 2002.

J. Schalwig et al., *"Group III-Nitride-Based Gas Sensors for Combustion Monitoring"*, Elsevier, materials Science and Engineering, B93, pp. 207-214, 2002..

Shinji Nakagomi et al., *"MISiC-FET Device With Bias Controlled Baseline and Gas Response"*, IEEE International Conference on Sensors, vol. 2, pp. 1168-1173, 2003.

A. Loyd Spetz et al., *"MISiCFET Sensor Arrays for On Line Diagnosis"*, IEEE International Conference on Sensors, vol. 2, pp. 1124-1125, 2003.

PCT International Search Report dated Feb. 7, 2005.

* cited by examiner

GAS SENSOR DEVICE

BACKGROUND OF INVENTION

The present disclosure relates to gas sensor devices. More particularly, the present disclosure relates to gas sensor devices for harsh environments.

Nitrogen oxides, or $NO_x$, is the generic term for a group of highly reactive gases, all of which contain nitrogen and oxygen in varying amounts. Many of the nitrogen oxides are colorless and odorless. However, one common pollutant, nitrogen dioxide ($NO_2$) along with particles in the air can often be seen as a yellowish or reddish-brown layer over many urban areas. Other oxides of nitrogen are also important species which may require detection and monitoring such as nitric oxide (NO) and nitrous oxide ($N_2O$).

Nitrogen oxides form when fuel is burned at high temperatures, as in a combustion process. Examples of sources of $NO_x$ are motor vehicles, electric utilities, and other industrial, commercial, and residential sources that burn fuels.

It is well known that in recent years, organizations like the EPA (Environmental Protection Agency) and the ICAO (International Civil Aviation Organization) have implemented regulations that limit the amount of pollutants emitted into the troposphere by fossil-fuel powered devices such as gas turbines, aircraft engines, trucks, and locomotives. For example, the EPA invoked a series of "tiered" regulations limiting the nitrogen oxide ($NO_x$) production, among other effluents, emitted from diesel locomotives. In 2000 (Tier 0), a diesel locomotive was allowed to emit 9.5 gm/hp-hr of $NO_x$ emissions. However in 2005 (Tier 2), such engines are limited to only 5.5 gm/hp-hr of nitrogen-based pollutant, approximately one half of Tier-0 concentrations. These stringent regulations have forced manufacturers to rapidly develop new low emissions combustion technologies. Additionally, the laws have also had a synergistic effect. Not only do manufacturers want to limit emissions, but employ the concentration of specific exhaust products to actively control the power-generation process. In other words, because the combustion of hydrocarbon-based fuels is truly a thermo-chemical process, the ideal engine "health monitor" is found in the effluent gases. Similar to modern automobiles that employ an oxygen sensor in the exhaust stream to control the fuel-to-air ratio, industrial power generation companies require related sensor technologies to control and diagnose engine performance, albeit on a larger scale.

$NO_x$ and other exhaust gas species are difficult to sense and control, especially in harsh environments such as automobile, diesel, aircraft, and locomotive exhaust streams; power generation; flue gases; gas turbines. Such harsh environments can often reach temperatures of 300 degrees Celsius (° C.) to 1,000° C. These environments also often have corrosive atmospheres containing gases such as hydrocarbons, $NO_x$, and $SO_x$. These harsh environments may have high vibrations and high pressures, alone or in combinations with the high temperatures and/or corrosive atmospheres. Current solid-state gas sensors cannot operate in these harsh environments unless supplementary cooling of the gas-sampling probe is provided. Other gas sensors that are electrochemical based are expensive and cannot withstand the high temperatures that are present in these harsh environments. These sensors often times do not offer the accuracy required to meet many of the EPA emission regulations. Most ceramic-based sensors have difficulty or do not function at all at temperatures below 500° C.

Accordingly, there is a need for gas sensor devices for sensing and monitoring exhaust gases and other harsh environment gases that can operate or withstand over a wide range of temperatures minimally from room temperature to above 600° C. Such gas sensors must have acceptable full-scale range, measurement resolution, and signal-to-noise ratio.

BRIEF DESCRIPTION OF THE INVENTION

The present disclosure provides a gas sensor device which includes a semiconductor layer having a surface and including a material selected from silicon carbide, diamond, Group III nitrides, alloys of Group III nitrides, zinc oxide, or any combinations thereof; one or more catalytic gate-electrodes deposited on the surface; one or more ohmic contacts deposited on the surface; and a passivation layer deposited on at least a portion of the surface.

The present disclosure also provides a gas sensor device which includes a semiconductor substrate having a surface and including a material selected from silicon carbide, diamond, Group III nitrides, alloys of Group III nitrides, zinc oxide, or any combinations thereof, the semiconductor substrate including at least one doped layer; one or more catalytic gate-electrodes deposited on the surface; one or more ohmic contacts deposited on the surface; a passivation layer deposited on at least a portion of the surface; and a means for encapsulating the gas sensor device.

The present invention further provides a gas sensor device which includes a semiconductor substrate having a surface, the semiconductor substrate including a material selected from silicon carbide, diamond, Group III nitrides, alloys of Group III nitrides, zinc oxide, or any combinations thereof; one or more catalytic gate-electrodes deposited on the surface; and one or more ohmic contacts deposited on the surface, the gas sensor being a flip-chip further having a layer of platinum or gold deposited on at least a portion of the one or more ohmic contacts and/or the one or more catalytic gate-electrodes.

The present invention still further provides a gas sensor device which includes a semiconductor substrate having a surface, the semiconductor substrate including a material selected from silicon carbide, diamond, Group III nitrides, alloys of Group III nitrides, zinc oxide, or any combinations thereof; an insulating layer; one or more catalytic gate-electrodes deposited on a surface of the insulating layer; and one or more ohmic contacts deposited on a surface of the semiconductor substrate, the gas sensor being a MISFET.

The present disclosure yet still further provides a gas sensor device which includes a semiconductor substrate having a heterostructure barrier layer and a surface, said semiconductor substrate comprising a material selected from silicon carbide, diamond, Group III nitrides, alloys of Group III nitrides, zinc oxide, or any combinations thereof; one or more catalytic gate-electrodes deposited on-the surface; one or more ohmic contacts deposited on the surface; and a passivation layer deposited on at least a portion of the surface underneath the one or more catalytic gate-electrodes, the gas sensor being a MISHFET.

DETAILED DESCRIPTION OF THE INVENTION

Figure 1:
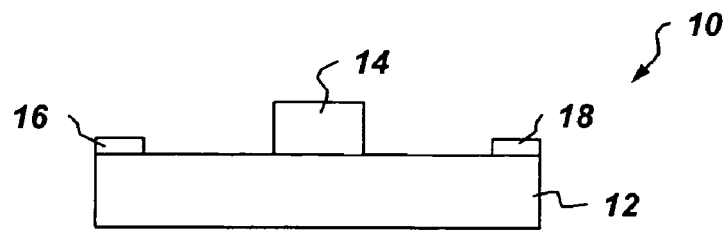
FIG. 1 shows a cross section of an example of a gas sensor device.

Gas sensor devices according to one embodiment of the present invention include a semiconductor layer having a surface, the semiconductor layer including a wide bandgap semiconductor material; one or more catalytic gate-electrodes deposited on the surface; and one or more ohmic contacts deposited on the surface.

The gas sensor devices can be used to sense the presence of, distinguish between, and measure concentration of a variety of gases. Examples of suitable gases to be sensed include, but are not limited to, NO, $NO_2$, $N_2O$, $NH_3$, CO, SO, $SO_2$, $SO_3$, $H_2$, hydrocarbons (HC), $CO_2$, and any combinations thereof.

The gas sensor devices of the present invention may be used to monitor gases in a variety of applications including, but not limited to, the emission of pollutants in the aluminum, cement, fertilizer, glass, mineral wool, power, steel, sulfuric acid, and waste incineration industries. The gas sensor devices may also be used to meet the U.S. Environmental Protection Agency continuous emission monitoring standards (CEMS) outlined in 40 C.F.R. § 60 and 40 C.F.R. § 75. The gas sensor devices may further be used to meet the European Union CEN emission limit values. Still further, the gas sensor devices may be used in a continuous emissions monitoring system to determine "cap and trade" allowances as described by local and federal regulating authorities.

Examples of suitable wide bandgap semiconductor materials include, but are not limited to, silicon carbide, diamond, Group III nitrides, alloys of Group III nitrides, zinc oxide and any combinations thereof. Examples of suitable Group III nitrides include, but are not limited to, GaN; InN; AlN; ternary alloys, such as AlGaN and InGaN; quaternary alloys, such as AlInGaN.

Wide bandgap semiconductor materials are capable of withstanding the temperatures and corrosive conditions of harsh environments. Further, these materials are cost effective in that they can be manufactured into devices on a large scale along the lines of well-established semiconductor devices. These materials provide chemically stable, thermally stable, repeatable responses in wide temperature ranges and harsh environments over a wide range of pressures. These materials are more robust (stable and reproducible) than Si and other conventional semiconductor materials in these harsh environments.

The substrate may include a heterostructure barrier layer. The heterostructure barrier layer may be deposited on the top of the semiconductor substrate material and may be in contact with the one or more catalytic gate-electrodes and/or one or more ohmic contacts. The heterostructure barrier layer improves the sensitivity of the gas sensor device to the gases. Without being bound to any particular theory, it is believed that the heterostructure barrier layer improves sensitivity due its very high sensitivity to shifts of charge carriers in the material as compared to conventional structures. The resistivity of the semiconductor device is dependent to a large degree on trapped charge from gases reacting with the catalyst at the surface.

The heterostructure barrier layer may be doped. Examples of materials suitable for doping a heterostructure barrier layer include, but are not limited to, silicon, magnesium, manganese, carbon, vanadium, titanium, aluminum, nitrogen, and any combinations thereof. The epitaxial layer of the semiconductor substrate may also be doped. Examples of materials suitable for doping an epitaxial layer include, but are not limited to, silicon, magnesium, manganese, carbon, vanadium, titanium, aluminum, nitrogen, and any combinations thereof. A heterostructure barrier layer, a epitaxial layer, both a heterostructure barrier layer and a epitaxial layer, or neither layer may be doped.

The gas sensor devices can be any device that senses gases in a harsh environment. Examples of suitable devices include, but are not limited to, a field effect transistor, a capacitor, a diode, and a resistor.

The arrangement of the components of the device can be such that the device is a heterostructure field effect transistor (HFET), a metal oxide semiconductor field effect transistor (MOSFET), a metal semiconductor field effect transistor (MESFET), a metal insulator semiconductor field effect transistor (MISFET), a metal insulator semiconductor heterostructure field effect transistor (MISHFET), or a Schottky diode.

The one or more catalytic gate-electrodes can include any material capable of reducing and/or oxidizing the species to be sensed. Examples of suitable materials for the one or more catalytic gate electrodes include, but are not limited to, metal, metal oxide, metal nitride, metal alloy, combination of metal oxides, and any combinations thereof. The one or more catalytic gate electrodes may also include a material of the formula $ABO_3$ where A is lanthanum and B is any transition metal or alkaline earth metal. The different catalytic materials possess different sensitivities to various gases. A sensor with one or more catalytic gate electrodes can, thus, detect multiple gases, distinguish between the gases, and determine concentrations of each of the gases depending on the selection and arrangement of the materials. Although, each sensor device may have one or more catalytic gate electrodes, an array of sensor devices each with one or more catalytic gate electrodes is also envisioned.

Catalytic metal materials are thermally and chemically stable at the higher temperatures of harsh environments and can interact with many gas species, including hydrocarbons therein. Examples of suitable metals include, but are not limited to, platinum, ruthenium, silver, palladium, iridium, indium, rhodium, titanium, aluminum, gold, nickel, rhenium, tantalum, osmium, and any combinations thereof. Catalytic metals may be combined as alloys. Examples of suitable metal alloys include, but are not limited to, platinum/rhodium, palladium/iridium, platinum/titanium/gold, platinum/ruthenium, platinum/iridium, platinum/gold, and any combinations thereof.

Catalytic oxide materials are also thermally and chemically stable at the higher temperatures of harsh environments and can interact with many gas species of interest. Metal oxide catalysts retain stability and sensitivity to gases, such as NOx, in harsh environments. Metal oxide catalysts are also stable to corrosives and poisons typically found in harsh environments and interact with hydrocarbons. Examples of suitable metal oxides include, but are not limited to, gallium oxide, silver oxide, indium oxide, vanadium oxide, $Ag_2O$, $Mn_2O_3$, CuO, $Cr_2O_3$, $Co_2O_3$, $Ga_2O_3$, $In_2O_3$, $V_2O_5$, ZnO, $Ge_2O_3$, $FeO_2$, bismuth molybdates, and any combinations thereof. Metal oxide-based oxidation catalysts are robust and, thus, retain stable response and sensitivity to gases in harsh environments. Further, for $NO_x$ sensing, oxidation catalysts allow the conversion of NO to $NO_2$, for which there is a significant signal sensitivity increase, for example when detected with an absorbent surface.

Metal oxides may be combined as combinations of oxides. The combinations of oxides may be part of a single layer of catalytic material. Examples of suitable combinations of oxides include, but are not limited to, platinum/tin oxide, platinum/indium oxide, zinc oxide/vanadium oxide, indium oxide/tin oxide/manganese oxide, and any combinations thereof.

The one or more catalytic gate-electrodes may be a multiple layer stack of catalytic material layers. Each of the catalytic material layers may include a single catalytic material or a combination/alloy of catalytic materials. Each of the catalytic material layers may be capable of sensing a different gas. A multiple layer stack of platinum, titanium, and gold is particularly robust in harsh environments.

Each layer of material in the one or more catalytic gate electrodes can have a thickness from about 50Å to about 8000Å, more preferably from about 100Å to about 5000Å, and most preferably from about 200Å to about 3000 Å.

The one or more ohmic contacts can include any material capable of physical and electrical contact to the device. Examples of suitable material for the one or more ohmic contacts includes, but are not limited to, titanium, aluminum, gold, nickel, chromium, indium, and any combinations thereof.

The one or more ohmic contacts may be a multiple layer stack of materials. Examples of suitable multiple layer stacks for the one or more ohmic contacts include, but are not limited to, titanium/aluminum/titanium/gold, titanium/aluminum, nickel, nickel/aluminum, nickel/chrome, indium, and any combinations thereof.

Each layer of material in the one or more ohmic contacts can have a thickness from about 100Å (Angstroms) to about 2000Å, more preferably from about 300Å to about 1500Å, and most preferably from about 500Å to about 1000 Å.

A passivation layer may be deposited on at least a portion of the device. This passivation layer may be interposed between the substrate and the one or more catalytic gate-electrodes. The passivation layer may improve the thermal stability and reproducibility of a gas sensor device. The passivation layer may be deposited via any known method. Examples of suitable deposition methods include, but are not limited to, plasma enhanced chemical vapor deposition (PECVD), pulsed laser deposition (PLD), low pressure chemical vapor deposition (LPCVD), and any combinations thereof. For one example, an LPCVD grown layer of silicon nitride or silicon dioxide may be deposited on a Group III nitride semiconductor substrate with the catalytic gate electrode deposited on top of the passivation layer. In this LPCVD example, ohmic contacts are deposited by first etching the passivation layer. In addition to acting as an effective passivation layer, the LPCVD deposited silicon nitride and/or silicon dioxide are highly stable in harsh environments and act to reduce gate leakage.

The passivation layer may include any material capable of reducing the number of free charge carriers present at the surface of the semiconductor, thereby minimizing device drift. Examples of suitable materials for the passivation layer include, but are not limited to, silicon nitride, silicon dioxide, MgO, $Sr_2O_3$, $ZrO_2$, $Ln_2O_3$, $TiO_2$, AlN, carbon, and any combinations thereof.

The passivation layer can have a thickness from about 100Å to about 8000Å, more preferably from about 250Å to about 5000Å, and most preferably from about 500Å to about 3000 Å.

A layer of an insulating material may be interposed between the semiconductor and one or more catalytic gate electrodes. Such insulating material may reduce the mobile ion damage and minimize drift in gas sensor devices. Examples of suitable insulating materials include, but are not limited to, polysilicate glass, silicon dioxide, silicon nitride, and any combinations thereof. This layer may also improve the physical adhesion of the catalyst material to the underlying layer (e.g. a semiconductor surface or passivation layer).

The gas sensor device may be encapsulated. The encapsulation further protects the device from the high temperature and corrosive atmosphere of the harsh environments. The encapsulant acts to tightly cover the ohmic contact metals and peripheral areas of the device which do not benefit from exposure to the gases. This coverage may also be enhanced by forming a bond with the underlying layer which does not permit the flow of gases or other corrosive molecules which would be a detriment to the device over time. Examples of suitable materials for encapsulating include, but are not limited to, silicon carbide, ceramic-based epoxies such as those containing alumina, glass, quartz, silicon nitride, silicon dioxide, and any combinations thereof. The encapsulation layer can be deposited by any known method, such as plasma enhanced chemical vapor deposition (PECVD), low pressure chemical vapor deposition (LPCVD), and any combinations thereof. The encapsulation is such that at least a portion of the one or more catalytic gate electrodes remains exposed to the ambient gases.

Advantageously, it has been found that utilizing wide bandgap materials, such as GaN and/or SiC with a passivation layer provides greater device stability, especially at elevated temperatures. The electronic properties of the devices are particularly important to control in highly sensitive devices, and with the addition of a passivation layer, this aspect may be significantly improved. Additionally, it has been found that by further adding the application of an encapsulation layer, these gas sensors are well suited for high temperatures, as well as offer protection from many of the potentially detrimental constituents present in harsh environments, such as exhaust gas applications. These include, but are not limited to, soot and other particulate matter resulting in unburned hydrocarbons and/or oil that get passed through the exhaust system. Such particulate matter could potentially be damaging to gas sensors applied directly in the stream as they may adhere to (and/or corrode) the surface of the device, and block the catalyst from the $NO_x$ in the exhaust stream. With the application of an encapsulant, the sensors may be protected and have a much longer life of operability. Thus, gas sensors capable of sensing gases in harsh environments find particular application in boiling water reactor exhaust gases, gas turbine exhaust gases, automotive and locomotive diesel engine exhaust, industrial process (glass, aluminum, steel, and petroleum) plant exhaust.

In another aspect, a gas sensor device is arranged within an encapsulation in a flip-chip arrangement. In a flip-chip arrangement, the gas sensor device is flipped upside down, such that all of the top surface areas of the device including the metal contacts, and the area surrounding the sensitive area of the device where the catalyst layers are placed, are protected from the gases to be monitored. An additional protective board protects the back surface of the chip. Directly over the sensitive area of the device, a slit, or opening in the ceramic board to which the chip's top surface is mounted, is created to allow the gases to flow to the catalyst for sensing. A layer of a high temperature stable conductive material, such as platinum or gold, may be used to interconnect the components of the gas sensor device to leads in the encapsulation layer. This flip-chip arrangement enables interconnect in a higher vibration and higher temperature, for example greater than 500° C., environment than conventional wire bonds, which are susceptible to fatigue failure. The interconnection using platinum and/or gold "bumps" to connect the components, such as the one or more ohmic contacts and/or the one or more catalytic gate-electrodes, of the gas sensor device to the leads helps to enable the use of the gas sensor device in the harsh environments.

In still another aspect, the gas sensor device is operable in an ambient environment ranging from about minus 40° C. to about 1000° C., more preferably from about 25° C. to about 800° C., and most preferably from about 25° C. to about 600° C. At these ambient conditions, the sensor retains the ability to sense a variety of gases, depending on the catalytic gate electrode material used.

In yet still another aspect, the gas sensor device may include a way of heating the gas device. A means for heating may be disposed around the epitaxial layer, underneath the semiconductor chip, on the package, and any combinations thereof. The heating means may be a separate element, such as a metal layer disposed directly in contact with the gas sensor device, or a thermoelectric heater disposed adjacent to the gas sensor device. The heating means may also be the gas sensing device itself. In one aspect, a large current may be passed through the gas sensor device in order to heat it to a desired temperature. The addition of heat, to the surface of the gas sensor device may result in faster response times and, thus, higher sensitivity. Not to be limited by to any particular theory, it is believed that the heat decreases the resident time of each gas species at the surface of the catalyst. The heating means may also allow for adjusting the temperature of the gas sensor device to allow for higher sensitivity to gas species that require higher temperatures for catalysis, even when the gas stream environment to be measured has not reached such temperatures. This may be important in such applications that require sensing when an engine has only recently been started. Keeping the gas sensor device at a constant temperature, such as the maximum operable temperature, can also be used to remove any signal dependence on temperature. Additionally, the heating of the sensor may be intentionally modified to provide a selective response to a variety of gases as driven by the catalyst's temperature dependence on reactivity to that species of gas.

In a further aspect, a gas sensor device may be packaged in any known packaging. Packaging may include a means for limiting or regulating the type and or amount of gas species that contact the one or more catalytic gate electrodes of the gas sensor device. Examples of suitable means for limiting or regulating the type and or amount of gas species include, but are not limited to, a thin film, such as Kapton or Teflon, over an entry hole, porous membrane filter medium (e.g. steel wool or quartz wool), and any combinations thereof. Packaging techniques in which arrays of gas sensor devices comprise different membrane materials provide for selectivity among various gases.

Referring to the drawings and in particular to FIG. 1, one example of a gas sensor device is illustrated by way of reference numeral 10. A semiconductor substrate 12 has thereon a catalytic gate electrode 14 and ohmic contacts 16 and 18.

Figure 2:
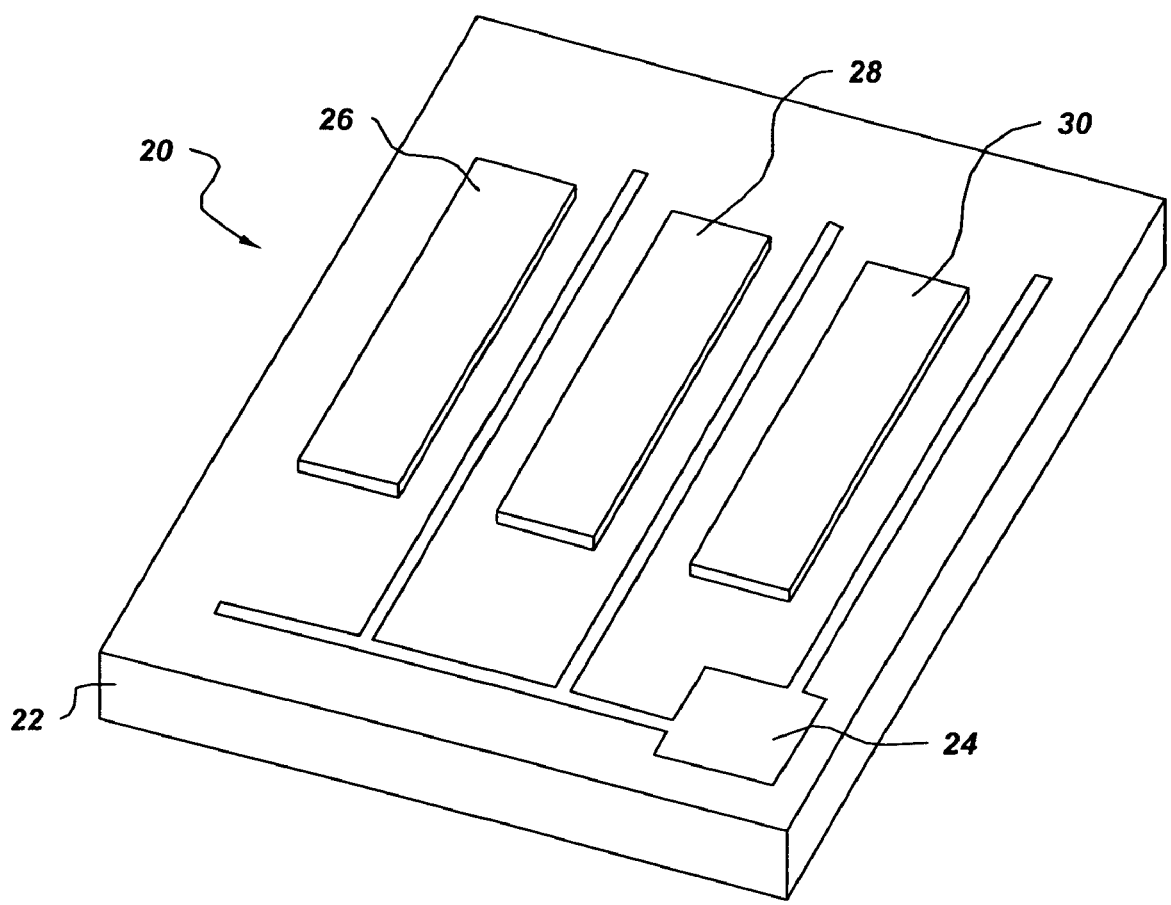
FIG. 2 shows a perspective view of an example of a gas sensor device.

FIG. 2 shows another example of a gas sensor device 20 with a semiconductor substrate 22, ohmic contact 24, and catalytic gate electrodes 26, 28, and 30. Using various catalytic materials for the gate electrodes 26, 28, and 30 can result in sensitivity to a combination of gases. Gas sensor devices capable of sensing a variety of gases simultaneously can provide for the real time monitoring of complex harsh environments.

EXAMPLE 1

Figure 3:
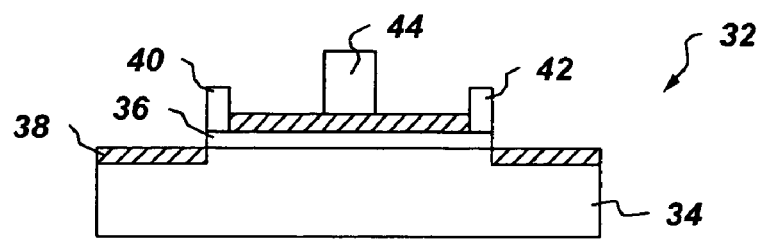
FIG. 3 shows a cross section of an example of a MISH-FET gas sensor device.

FIG. 3 shows one example of a gas sensor device 32 in a MISHFET configuration. In this example of a MISHFET configuration an undoped GaN substrate 34 includes an undoped AlGaN heterostructure barrier layer 36 thereon. It should be understood that these semiconductor materials may be substituted with any of the wide bandgap materials discussed above, for example binary and ternary Group III nitrides. The substrate 34 and heterostructure barrier layer 36 in this example have been patterned using photolithography and etched using inductively coupled plasma-enhanced reactive ion etching (ICP-RIE), which is a specially enhanced method of dry etching robust materials such as GaN and SiC and is widely known to those practicing the art of semiconductor processing. A passivation layer 38, such as a LPCVD grown silicon nitride and/or silicon dioxide, is deposited. The passivation layer 38 is etched from regions where ohmic contacts 40 and 42 will be deposited. Ohmic contacts 40 and 42, such as a multiple layer stacks of a layer of titanium (Ti), a layer of aluminum (Al), a layer of Ti, and a layer of gold (Au) (200 Å/1000 Å/450 Å/550 Å), are deposited and annealed, for example at a temperature of about 800° C. for about 60 seconds. A catalytic gate electrode 44, such as a multiple layer stack of a single layer of platinum (Pt), a layer of Ti, a layer of Al, and a layer of Au (500 Å/200 Å/500 Å/5000 Å), is deposited on the passivation layer 38. MISHFET gas sensor devices, such as this example, are provide high stability and reproducibility at high temperatures, such as greater than 400° C. and in harsh environments. It should also be noted that although this example shows a single catalytic gate electrode, one or more catalytic gate electrodes may be part of each gas sensor device and/or an array of gas sensor devices may be employed.

In another example, the gas sensor device 32 in FIG. 3 can represent a MISFET device by removing the heterostructure barrier layer 36 and having feature 44 be an insulating layer, such as silicon dioxide or silicon nitride.

Example 2

Figure 4:
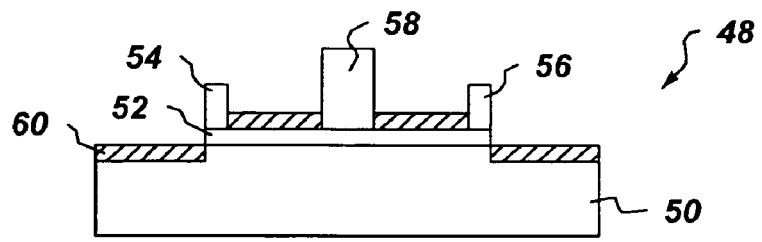
FIG. 4 shows a cross section of an example of a HFET gas sensor device.

FIG. 4 shows another example of a gas sensor device 48 in a HFET configuration. In this example of an HFET configured gas sensor device an undoped GaN substrate 50 includes an undoped AlGaN heterostructure barrier layer 52. It should be understood that these semiconductor materials may be substituted with any of the wide bandgap materials discussed above, for example binary and ternary Group III nitrides. The substrate 50 and heterostructure barrier layer 52 have been patterned using photolithography and etched using ICP-RIE. Ohmic contacts 54 and 56, such as multiple layer stacks of a layer of Ti, a layer of Al, a layer of Ti, and a layer of Au (200 Å/1000 Å/450 Å/550 Å) are deposited on the heterostructure barrier layer 52. The ohmic contacts may be annealed at about 800° C. for about 60 seconds. A catalytic gate electrode 58, such as a multiple layer stack of a layer of Pt, a layer of Ti, a layer of Al, and a layer of Au (500 Å/200 Å/500 Å/5000 Å), is deposited on the heterostructure barrier layer 52. A passivation layer 60, such as a silicon nitride, is deposited on the device. It should also be noted that although this example shows a single catalytic gate electrode, one or more catalytic gate electrodes may be part of each gas sensor device and/or an array of gas sensor devices may be employed.

Example 3

Figure 5:
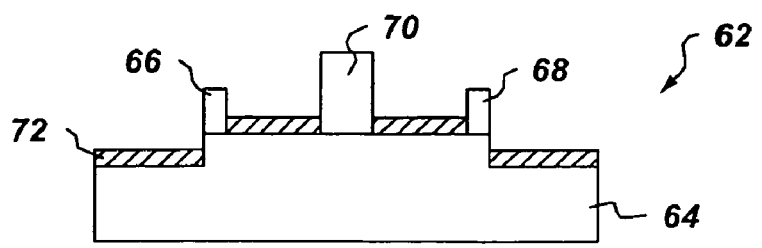
FIG. 5 shows a cross section of an example of a Schottky Diode gas sensor device.

FIG. 5 shows yet another example of a gas sensor device 62 in a Schottky diode configuration. In this example of a Schottky diode configured gas sensor device a doped GaN substrate 64 has been patterned using photolithography and etched using ICP-RIE. It should be understood that these semiconductor materials may be substituted with any of the wide bandgap materials discussed above, for example AlGaN, AlInN and silicon carbide. Ohmic contacts 66 and 68, such as multiple layer stacks of a layer of Ti, a layer of Al, a layer of Ti, and a layer of Au (200 Å/1000 Å/450 Å/550 Å) is deposited on the substrate 64. The ohmic contacts may be annealed at about 800° C. for about 60 seconds. A catalytic gate electrode 70, such as a multiple layer stack of a layer of Pt, a layer of Ti, a layer of Al, and a layer of Au (500 Å/200 Å/500 Å/5000 Å), is deposited on the substrate 64. A passivation layer 72, such as a silicon nitride, is deposited on the device. It should also be noted that although this example shows a single catalytic gate electrode, one or more catalytic gate electrodes may be part of each gas sensor device and/or an array of gas sensor devices may be employed.

Example 4

Figure 6:
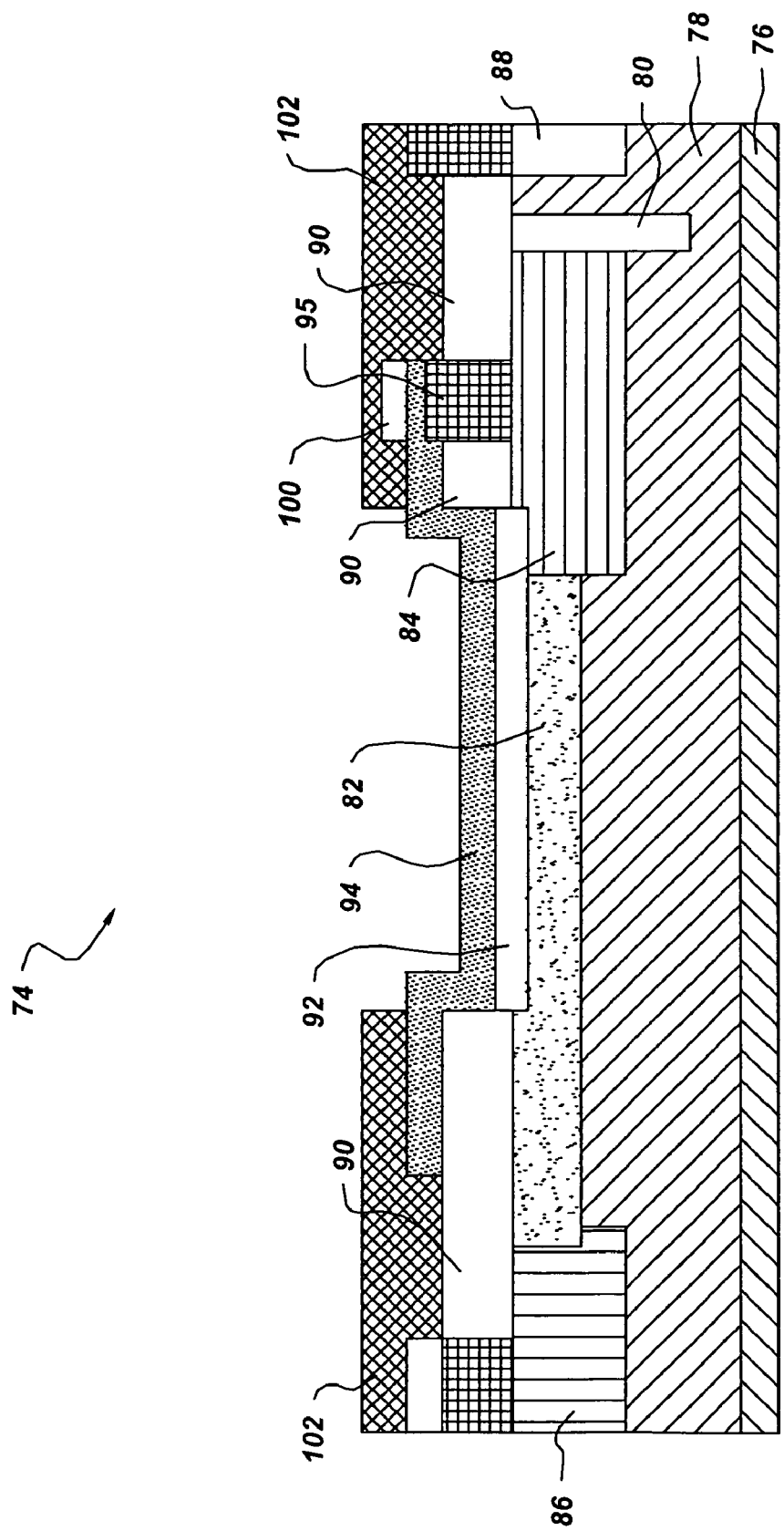
FIG. 6 shows a cross section of an example of a MOSFET gas sensor device.

FIG. 6 shows still yet another example of a gas sensor device in a MOSFET configuration. In this example of a MOSFET configured gas sensor device, a silicon carbide n-type substrate 76 has thereon a P-epitaxial layer 78, such as 5e1 5 p-type epitaxial layer of 4 micrometers (μm) thickness. A mesa 80 is etched by depositing a resist, imaging, patterning, etching the epitaxial layer 56, and stripping the resist. An n-channel 92 is implanted by depositing and densifying 1 μm HTO oxide layers, using photoresist mask and RIE etch oxide, depositing screen oxide, implanting in the epitaxial layer 78 an n-channel 82 using 3 implants to get a box profile at 600° C., 180 KeV, n ions, and stripping the oxide. An N+ source 84 and an N+ drain 86 are implanted by depositing and densifying 1 μm HTO oxide layers, using photoresist mask and RIE etch oxide, depositing screen oxide, implanting in the epitaxial layer 78 an N+ source 84 and an N+ drain 86 using 3 implants to get a box profile at 600° C., n ions, and stripping the oxide. A P+ implant 88 for top or body contact is ion implanted by depositing and densifying 1 μm HTO oxide layers, using photoresist mask and RIE etch oxide, depositing screen oxide, implanting in the epitaxial layer 78 a P+ contact 88 using 4 implants to get a box profile at 1000° C., 180 KeV, Al and/or C ions, and stripping the oxide. The implants 82, 84, 86, and 88 are then annealed at 1,300° C. Sacrificial oxidation may be required for removing surface damage. A field oxide layer 90, such as $SiO_2$, is grown by thermal oxidation at 300 Angstroms, depositing and densifying 1 μm HTO oxide and phosphorous silicate glass (PSG), photoresist patterning, ICP etch (80%), and wet etch (20%) in channel. The field oxide 90 helps to protect the surface of the gas sensor device. A gate oxide 92, such as a high quality $SiO_2$, is grown by 1,100° C. steam oxidation (500 Angstroms), 950° C. steam re-oxidation anneal. A gate metal 94, such as nickel or molybdenum, is deposited by photopatterning, evaporating or sputtering about 4000 Angstroms of gate metal, and removing photoresist. Ohmic contacts, such as nickel and/or gold, are deposited using photopatterning with oxide etchback, evaporating or sputtering the nickel and/or gold, and liftoff of metal. A P-ohmic, such as Ti/Al and/or Ni/Al is deposited using photopatterning with oxide etchback, evaporating/sputtering Ti/Al and/or Ni/Al layers on top of P+ contact 88, lifting off metal, annealing ohmics at 975° C. ($N_2$ and/or Ar atmosphere for about 2 minutes). Gate metal 94 is deposited by photopatterning, evaporating/sputtering 300 Angstroms of catalytic gate electrode material, stripping photoresist, and annealing at 600° C. to activate catalyst. Overlay 100, such as Ti/Ni/Au is deposited using photopatterning, evaporating Ti/Ni/Au, and stripping the photoresist. A passivation layer 102 is deposited. It should also be noted that although this example shows a single catalytic gate electrode, one or more catalytic gate electrodes may be part of each gas sensor device and/or an array of gas sensor devices may be employed.

Example 5

Figure 7:
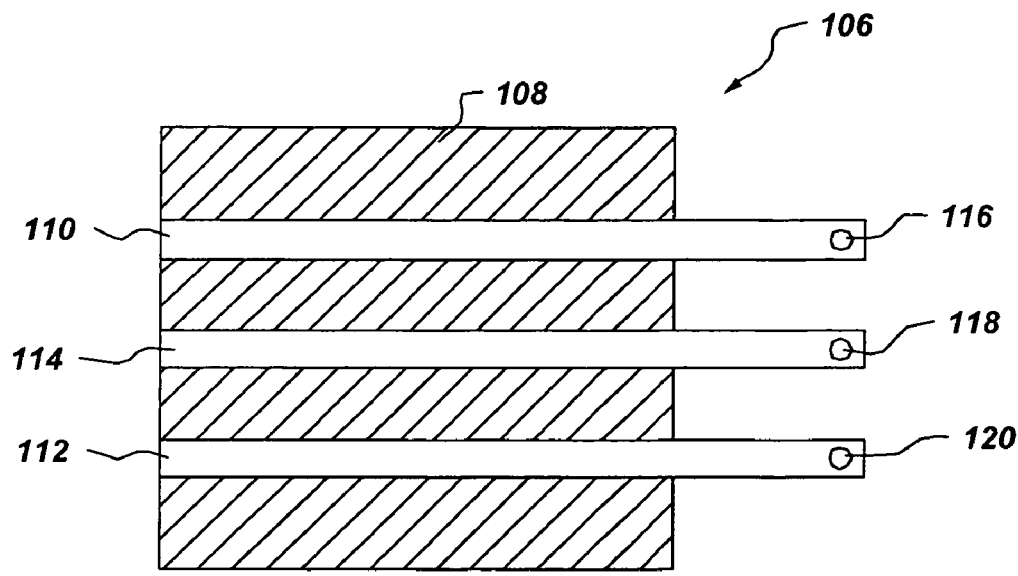
FIG. 7 shows a top view of an example of a gas sensor device having platinum bump interconnects.

FIG. 7 shows a top view of a further example of a gas sensor device 106 having a passivation layer 108 and platinum bumps 116, 118, and 120 for interconnection. The platinum bumps 116, 118, and 120 are deposited on the ohmic contacts 110 and 112 and the catalytic gate electrode 114. It should be noted that platinum bump interconnects may be on only the ohmic contacts, only the catalytic gate electrodes, or both. It should also be noted that although this example shows a single catalytic gate electrode, one or more catalytic gate electrodes may be part of each gas sensor device and/or an array of gas sensor devices may be employed.

Example 6

Figure 8:
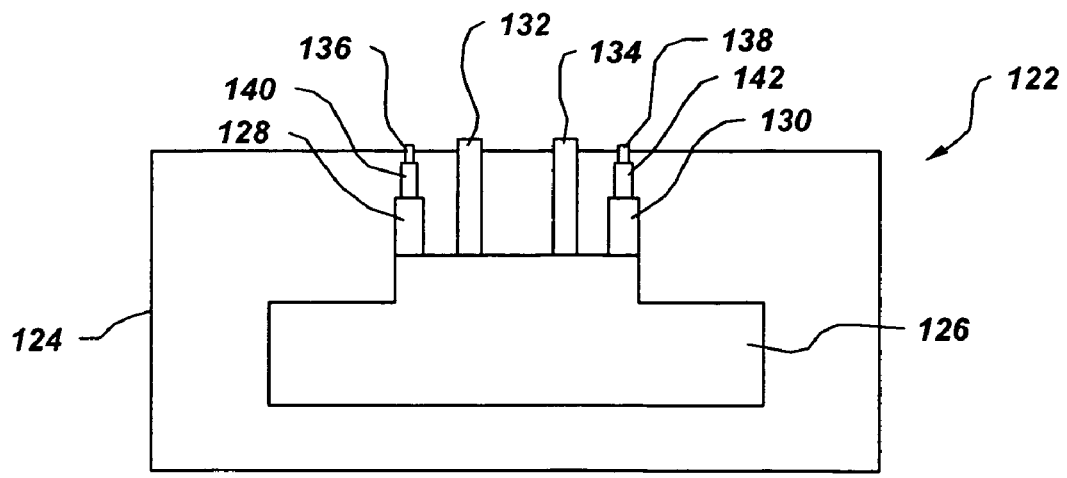
FIG. 8 shows a cross section of an example of a flip-chip gas sensor device.

FIG. 8 shows still a further example of a gas sensor device 122 with an encapsulation means 124. A substrate 126 has thereon ohmic contacts 128 and 130 and two catalytic gate electrodes 132 and 134. The catalytic gate electrodes 132 and 134 are exposed on the outside of the encapsulation means such that gas species may come in contact with the catalytic materials. This example also shows a flip-chip arrangement having interconnection of the ohmic contacts 128 and 130 to the leads 136 and 138 by platinum bumps 140 and 142. It should also be noted that although this example shows a dual catalytic gate electrode, one or more catalytic gate electrodes may be part of each gas sensor device and/or an array of gas sensor devices may be employed.

Example 7

Figure 9:
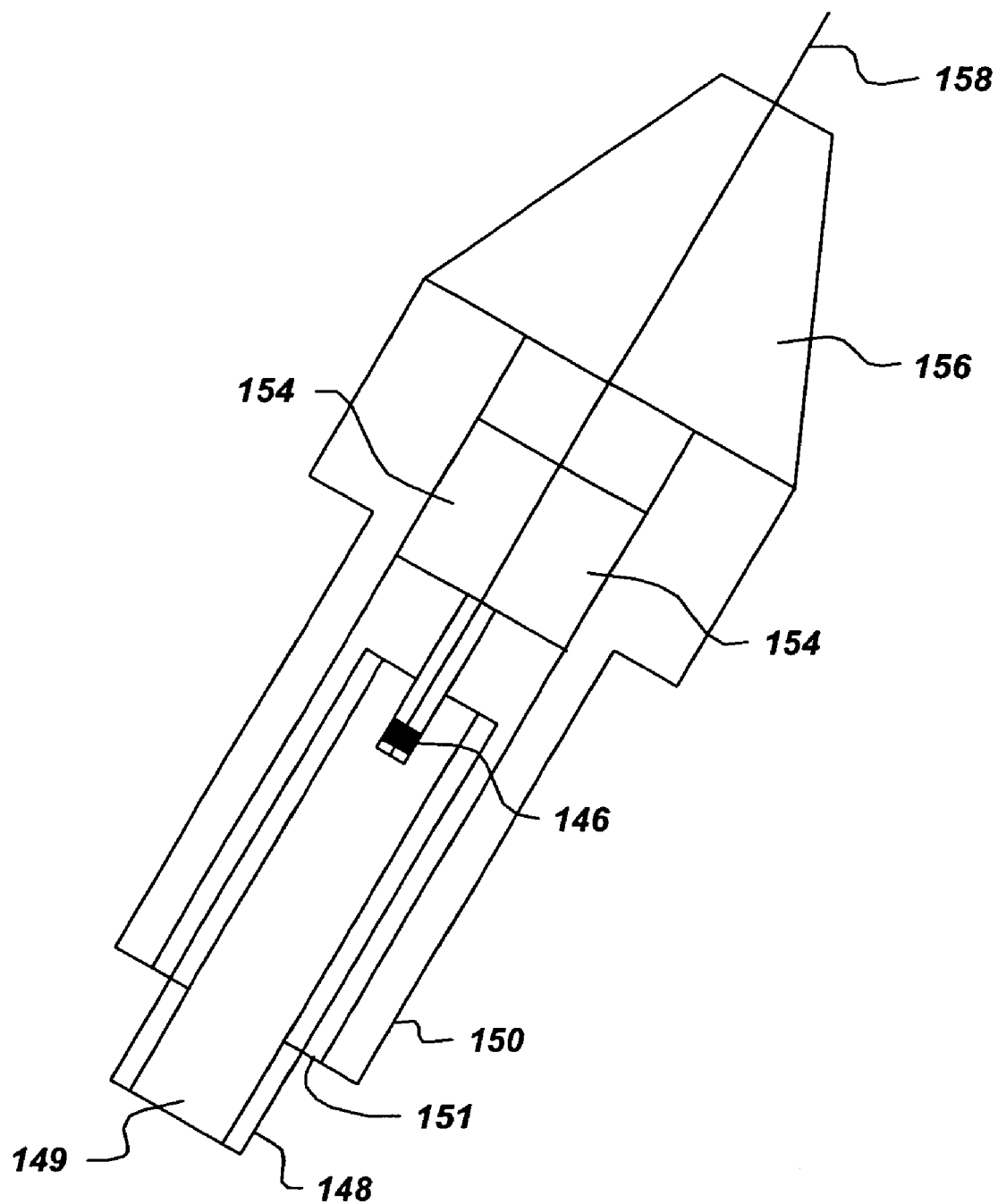
FIG. 9 shows an example of packaging for an example gas sensor device.

FIG. 9 shows one example of packaging 144 for an example of a gas sensor device 146. The gas sensor device 146 is disposed within a first tube 148. The first tube 148 is disposed within a second tube 150 such that gas species may pass in through a first void 149 in the first tube 148, past the gas sensor device 146, and out through a second void 151 between the first tube 148 and the second tube 150. The direction of the gas may also flow in the opposite direction. The packaging 144 also includes a substrate 152, thermal barrier 154, shroud 156, and signal connection 158.

Figure 10:
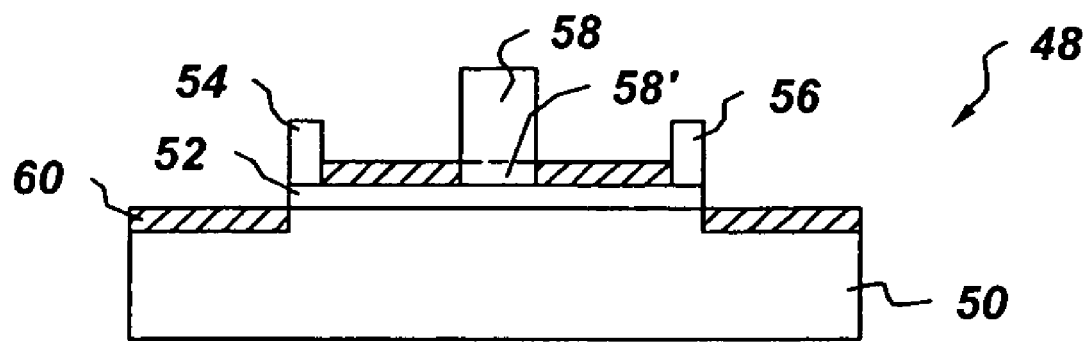
FIG. 10 shows a MISHFET gas sensor device in accordance with an embodiment of the invention.

FIG. 10 illustrates MISHFET a gas sensor device 48' in accordance with an embodiment of the invention. The gas sensor device 48' is similar in structure to the gas sensor device 48 (FIG. 4), except in the make-up of the catalytic gate-electrode. Specifically, the catalytic gate-electrode 58 illustrated in FIG. 10 includes a layer 58' of a metal oxide. The layer 58' serves as both a catalytic component and as an insulating component. The metal oxide making up the layer 58' may include any metal oxide suitable for serving as both a catalyst and an insulator, including those selected from the group consisting of gallium oxide, silver oxide, indium oxide, vanadium oxide, $Mn_2O_3$, CuO, $Cr_2O_3$, $Co_2O_3$, ZnO, $Ge_2O_3$, $FeO_2$, bismuth molybdates, and any combinations thereof. The combination of the catalytic gate-electrode 58, including the combined catalytic and insulating portion 58', and the heterostructure barrier layer 52 within the semiconductor substrate 50 forms a metal insulator semiconductor heterojunction field effect transistor (MISHFET).

Figure 11:
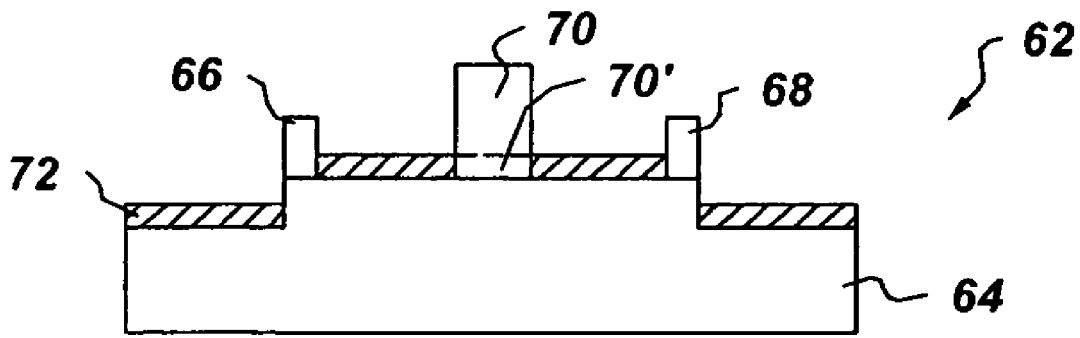
FIG. 11 shows a MISFET gas sensor device in accordance with an embodiment of the invention.

FIG. 11 illustrates a gas sensor device 62' in accordance with an embodiment of the invention. The gas sensor device 62' is similar in structure to the gas sensor device 62 (FIG. 5), except in the make-up of the catalytic gate-electrode. Specifically, the catalytic gate-electrode 70 illustrated in FIG. 10 includes a layer 70' of a metal oxide. The layer 70' serves as both a catalytic component and as an insulating component. The metal oxide making up the layer 70' may include any metal oxide suitable for serving as both a catalyst and an insulator, including those selected from the group consisting of gallium oxide, silver oxide, indium oxide, vanadium oxide, $Mn_2O_3$, CuO, $Cr_2O_3$, $Co_2O_3$, ZnO, $Ge_2O_3$, $FeO_2$, bismuth molybdates, and any combinations thereof. The combination of the catalytic gate-electrode 70, including the combined catalytic and insulating portion 70', and the semiconductor substrate 64 forms a metal insulator semiconductor field effect transistor (MISFET). The presence of metal oxide within the layer 70' also allows the gas sensor device 62' to be considered a metal oxide semiconductor field effect transistor (MOSFET).

It should be noted that although the examples above may use specific substrate materials, catalytic gate electrode materials, ohmic contact materials, and other specified materials, different variations of these materials may be employed.

It should also be noted that the terms "first", "second", "third", "upper", "lower", and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated for carrying out this disclosure, but that the disclosure will include all embodiments falling within the scope of the appended claims.

What is claimed is:

1. A gas sensor device comprising:
   a semiconductor layer having a surface, said semiconductor layer comprising a material selected from the group consisting of silicon carbide, diamond, Group III nitrides, alloys of Group III nitrides, zinc oxide, and any combinations thereof;
   one or more catalytic gate-electrodes contacting said surface;
   one or more ohmic contacts deposited on said surface; and
   a passivation layer covering only at least a portion of said surface;
   wherein the gas sensor device is selected from the group consisting of a HFET, a MISFET, a MOSFET, and a MISHFET.

2. The device of claim 1, wherein said semiconductor layer comprises a material selected from the group consisting of silicon carbide, gallium nitride, aluminum gallium nitride, and any combinations thereof.

3. The device of claim 1, wherein said one or more catalytic gate-electrodes comprises a material selected from the group consisting of metal, metal oxide, metal alloy, combination of metal oxides, and any combinations thereof.

4. The device of claim 3, wherein said metal is selected from the group consisting of platinum, ruthenium, silver, palladium, iridium, indium, rhodium, titanium, aluminum, gold, nickel, rhenium, tantalum and osmium, and any combinations thereof.

5. The device of claim 3, wherein said metal is selected from the group consisting of tantalum, osmium, and any combinations thereof.

6. The device of claim 3, wherein said metal oxide is selected from the group consisting of gallium oxide, silver oxide, indium oxide, vanadium oxide, $Mn_2O_3$, CuO, $Cr_2O_3$, $Co_2O_3$, ZnO, $Ge_2O_3$, $FeO_2$, bismuth molybdates, and any combinations thereof.

7. The device of claim 3, wherein said metal alloy is selected from the group consisting of platinum/rhodium, palladium/iridium, platinum/titanium/gold, platinum/ruthenium, platinum/iridium, platinum/gold, and any combinations thereof.

8. The device of claim 3, wherein said combination of oxides is selected from the group consisting of platinum/tin oxide, platinum/indium oxide, zinc oxide/vanadium oxide, indium oxide/tin oxide/manganese oxide, and any combinations thereof.

9. The device of claim 1, wherein said one or more catalytic gate-electrodes comprises a material of the formula $ABO_3$ where A is lanthanum and B is any transition metal or alkaline earth metal.

10. The device of claim 1, wherein said one or more ohmic contacts comprises a material selected from the group consisting of titanium, aluminum, gold, nickel, chromium, indium, and any combinations thereof.

11. The device of claim 1, wherein said one or more catalytic gate electrodes are uncovered by said passivation layer.

12. The device of claim 1, wherein said passivation layer comprises a material selected from the group consisting of silicon nitride, silicon dioxide, MgO, $Sr_2O_3$, $ZrO_2$, $Ln_2O_3$, $TiO_2$, AlN, carbon, and any combinations thereof.

13. The device of claim 1, wherein said semiconductor layer comprises a heterostructure barrier layer.

14. The device of claim 1, wherein said semiconductor layer comprise at least one layer that is doped.

15. The device of claim 1, further comprising a means for encapsulation.

16. The device of claim 1, wherein the gas sensor is a flip-chip further comprising a layer of platinum and/or gold deposited on at least a portion of said one or more ohmic contacts and for said one or more catalytic gate-electrodes.

17. The device of claim 1, wherein the gas sensor is operable in an ambient environment ranging from about minus 40° C. to about 800° C.

18. The device of claim 1, further comprising a means for heating.

19. The device of claim 1, wherein the gas sensor is capable of sensing a gas selected from the group consisting of: NO, $NO_2$, $N_2O$, $NH_3$, CO, SO, $SO_2$, $SO_3$, $CO_2$, $O_2$, Hz, hydrocarbons and any combinations thereof.

20. The device of claim 1, wherein each of the one or more catalytic gate electrodes senses a different gas.

21. The device of claim 1, wherein each of said one or more catalytic gate electrodes is a stack of catalytic material layers, each of said catalytic material layers comprising a material selected from the group consisting of metal, metal oxide, metal alloy, combination of metal oxides, and any combinations thereof.

22. A gas sensor device comprising:
a semiconductor substrate having a surface, said semiconductor substrate comprising a material selected from the group consisting of silicon carbide, diamond, Group III nitrides, alloys of Group III nitrides, zinc oxide, and any combinations thereof and comprising at least one doped layer;
one or more catalytic gate-electrodes contacting said surface;
one or more ohmic contacts deposited on said surface;
a passivation layer covering only at least a portion of said surface; and
means for encapsulating the gas sensor device;
wherein the gas sensor device is selected from the group consisting of a HFET, a MISFET, a MOSFET, and a MISHFET.

23. The device of claim 22, wherein said semiconductor layer comprises a material selected from the group consisting of silicon carbide, gallium nitride, aluminum gallium nitride, and any combinations thereof.

24. The device of claim 22, wherein said one or more catalytic gate-electrodes comprises a material selected from the group consisting of metal, metal oxide, metal alloy, combination of metal oxides, and any combinations thereof.

25. The device of claim 24, wherein said metal is selected from the group consisting of platinum, ruthenium, silver, palladium, iridium, indium, rhodium, titanium, aluminum, gold, nickel, rhenium, tantalum and osmium, and any combinations thereof.

26. The device of claim 24, wherein said metal is selected from the group consisting of tantalum, osmium, and any combinations thereof.

27. The device of claim 24, wherein said metal oxide is selected from the group consisting of gallium oxide, silver oxide, indium oxide, vanadium oxide, $Mn_2O_3$, CuO, $Cr_2O_3$, $Co_2O_3$, ZnO, $Ge_2O_3$, $FeO_2$, bismuth molybdates, and any combinations thereof.

28. The device of claim 24, wherein said metal alloy is selected from the group consisting of platinum/rhodium, palladium/iridium, platinum/titanium/gold, platinum/ruthenium, platinum/iridium, platinum/gold, and any combinations thereof.

29. The device of claim 24, wherein said combination of oxides is selected from the group consisting of platinum/tin oxide, platinum/indium oxide, zinc oxide/vanadium oxide, indium oxide/tin oxide/manganese oxide, and any combinations thereof.

30. The device of claim 22, wherein said one or more catalytic gate-electrodes comprises a material of the formula $ABO_3$ where A is lanthanum and B is any transition metal or alkaline earth metal.

31. The device of claim 22, wherein said one or more ohmic contacts comprises a material selected from the group consisting of titanium, aluminum, gold, nickel, and any combinations thereof.

32. The device of claim 22, wherein said passivation layer comprises a material selected from the group consisting of silicon nitride, silicon dioxide, MgO, Sr2O3, $ZrO_2$, $Ln_2O_3$, $TiO_2$, and any combinations thereof.

33. The device of claim 22, wherein said semiconductor layer comprises a heterostructure barrier layer.

34. The device of claim 22, further comprising a layer of platinum and/or gold deposited on at least a portion of said one or more ohmic contacts and/or said one or more catalytic gate-electrodes.

35. The device of claim 22, wherein said device is operable in an ambient environment ranging from about minus 40° C. to about 800° C.

36. The device of claim 22, wherein the gas sensor is a flip-chip further comprising a layer of platinum or gold deposited on at least a portion of said one or more ohmic contacts and/or said one or more catalytic gate-electrodes.

37. The device of claim 22, further comprising a means for heating.

38. The device of claim 22, wherein the gas sensor is capable of detecting a gas selected from the group consisting of: NO, $NO_2$, $N_2O$, $NH_3$, CO, SO, $SO_2$, $SO_3$, $CO_2$, $O_2$, $H_2$, hydrocarbons and any combinations thereof.

39. The device of claim 22, wherein each of the one or more catalytic gate electrodes senses a different gas.

40. The device of claim 22, wherein each of said one or more catalytic gate electrodes is a stack of catalytic material layers, each of said catalytic material layers comprising a material selected from the group consisting of metal, metal oxide, metal alloy, combination of metal oxides, and any combinations thereof.

41. A gas sensor device comprising:
a semiconductor substrate having a surface, said semiconductor substrate comprising a material selected from the group consisting of silicon nitride, silicon carbide, diamond, Group III nitrides, alloys of Group III nitrides, zinc oxide, and any combinations thereof;
one or more catalytic gate-electrodes contacting said surface; and
one or more ohmic contacts deposited on said surface;
a passivation layer covering only at least a portion of said surface;
a layer of platinum or gold deposited on at least a portion of said one or more ohmic contacts and/or said one or more catalytic gate-electrodes;
wherein the gas sensor device is a flip-chip device and wherein the gas sensor device is selected from the group consisting of a HFET, a MISFET, a MOSFET, and a MISHFET.

* * * * *